United States Patent
Bredno et al.

(10) Patent No.: US 10,898,222 B2
(45) Date of Patent: Jan. 26, 2021

(54) ADAPTIVE CLASSIFICATION FOR WHOLE SLIDE TISSUE SEGMENTATION

(71) Applicant: Ventana Medical Systems, Inc., Tucson, AZ (US)

(72) Inventors: Joerg Bredno, San Francisco, CA (US); Christophe Chefd'hotel, San Jose, CA (US); Ting Chen, Sunnyvale, CA (US); Srinivas Chukka, San Jose, CA (US); Kien Nguyen, Ho Chi Minh (VN)

(73) Assignee: VENTANA MEDICAL SYSTEMS, INC., Tucson, AZ (US)

(*) Notice: Subject to any disclaimer, the term of this patent is extended or adjusted under 35 U.S.C. 154(b) by 209 days.

(21) Appl. No.: 16/130,958

(22) Filed: Sep. 13, 2018

(65) Prior Publication Data

US 2019/0038310 A1    Feb. 7, 2019

Related U.S. Application Data

(63) Continuation of application No. 15/222,889, filed on Jul. 28, 2016, now Pat. No. 10,102,418, which is a (Continued)

(51) Int. Cl.
*A61B 17/34* (2006.01)
*G06K 9/46* (2006.01)
(Continued)

(52) U.S. Cl.
CPC .......... *A61B 17/3415* (2013.01); *A61B 1/018* (2013.01); *A61B 17/00234* (2013.01);
(Continued)

(58) Field of Classification Search
None
See application file for complete search history.

(56) References Cited

U.S. PATENT DOCUMENTS

| | | | |
|---|---|---|---|
| 5,912,986 A * | 6/1999 | Shustorovich | G06K 9/32 382/156 |
| 6,760,468 B1 * | 7/2004 | Yeh | G06F 19/345 128/922 |

(Continued)

FOREIGN PATENT DOCUMENTS

| | | | |
|---|---|---|---|
| WO | 2010138121 A1 | 12/2010 | |
| WO | WO-2010138121 A1 * | 12/2010 | ........... G06K 9/4671 |
| WO | 2012058217 A2 | 5/2012 | |

OTHER PUBLICATIONS

Azmi, R., Pishgoo, B., Norozi, N., & Yeganeh, S. (2013). Ensemble semi-supervised frame-work for brain magnetic resonance imaging tissue segmentation. Journal of medical signals and sensors, 3(2), 94. (Year: 2013).*

(Continued)

*Primary Examiner* — Samah A Beg
(74) *Attorney, Agent, or Firm* — Kilpatrick Townsend & Stockton LLP

(57) ABSTRACT

A method of segmenting images of biological specimens using adaptive classification to segment a biological specimen into different types of tissue regions. The segmentation is performed by, first, extracting features from the neighborhood of a grid of points (GPs) sampled on the whole-slide (WS) image and classifying them into different tissue types. Secondly, an adaptive classification procedure is performed where some or all of the GPs in a WS image are classified using a pre-built training database, and classification confidence scores for the GPs are generated. The classified GPs with high confidence scores are utilized to generate an adaptive training database, which is then used to re-classify the low confidence GPs. The motivation of the method is that the strong variation of tissue appearance makes the classification problem more challenging, while (Continued)

---

Algorithm 1 Adaptive classification

Input: Pre-built training DB $\Theta$, test data $\Gamma$, confidence threshold $\delta_c$.
Output: Classification result, $L = \{l(x_i) \in T \; \forall x_i \in \Gamma\}$.

1: Build a classifier $\mathcal{F}$ using $\Theta$.
2: Apply $\mathcal{F}$ to each $x_i$, obtain a label $l(x_i)$, and a confidence score $c(x_i) \in [0, 1]$.
3: Find high confidence samples, $x^h = \{x_i | c(x_i) \geq \delta_c\}$, and low confidence samples $x^l = \{x_i | c(x_i) < \delta_c\}$. Let $\Delta = \{(x_i, l(x_i)), | x_i \in x^h\}$
4: Generate an adaptive training DB $\Theta^*$ by combining $\Theta$ and $\Delta$ using Algorithm 2. In Algorithm 2, we consider $\Theta$ as the external training DB, and $\Delta$ as the internal training DB.
5: Learn a classifier $\mathcal{F}^*$ using $\Theta^*$.
6: Use $\mathcal{F}^*$ to re-classify samples in $x^l$ to obtain $\{l^*(x_i) | x_i \in x^l\}$.
7: Create $L = \{l(x_i) | x_i \in x^h\} \cup \{l^*(x_i) | x_i \in x^l\}$ good classification results are obtained when the training and test data origin from the same slide.

24 Claims, 10 Drawing Sheets

Related U.S. Application Data continuation of application No. PCT/EP2015/051302, filed on Jan. 23, 2015.

(60) Provisional application No. 61/932,671, filed on Jan. 28, 2014, provisional application No. 62/033,261, filed on Aug. 5, 2014.

(51) Int. Cl.

| | |
|---|---|
| *G06K 9/62* | (2006.01) |
| *G06K 9/66* | (2006.01) |
| *G06T 7/00* | (2017.01) |
| *G06T 7/73* | (2017.01) |
| *G06T 7/11* | (2017.01) |
| *G06K 9/00* | (2006.01) |
| *G06T 7/40* | (2017.01) |
| *A61B 34/00* | (2016.01) |
| *A61B 1/018* | (2006.01) |
| *A61B 17/00* | (2006.01) |
| *A61B 1/12* | (2006.01) |
| *B33Y 10/00* | (2015.01) |
| *B33Y 80/00* | (2015.01) |

(52) U.S. Cl.
CPC .......... *A61B 17/3423* (2013.01); *A61B 34/71* (2016.02); *A61B 34/74* (2016.02); *G06K 9/00147* (2013.01); *G06K 9/4642* (2013.01); *G06K 9/4652* (2013.01); *G06K 9/623* (2013.01); *G06K 9/66* (2013.01); *G06T 7/0012* (2013.01); *G06T 7/11* (2017.01); *G06T 7/40* (2013.01); *G06T 7/74* (2017.01); *A61B 1/126* (2013.01); *A61B 2017/00261* (2013.01); *A61B 2017/00477* (2013.01); *A61B 2017/00526* (2013.01); *A61B 2017/3445* (2013.01); *A61B 2034/715* (2016.02); *A61B 2034/742* (2016.02); *B33Y 10/00* (2014.12); *B33Y 80/00* (2014.12); *G06T 2207/20081* (2013.01); *G06T 2207/30024* (2013.01)

(56) References Cited

U.S. PATENT DOCUMENTS

| | | | | |
|---|---|---|---|---|
| 2004/0202368 | A1* | 10/2004 | Lee | G06K 9/00624 382/173 |
| 2013/0030281 | A1* | 1/2013 | Suri | A61B 6/03 600/410 |
| 2013/0156280 | A1* | 6/2013 | Kadir | G06T 7/0012 382/128 |
| 2013/0346346 | A1* | 12/2013 | Criminisi | G06N 99/005 706/12 |
| 2014/0247972 | A1* | 9/2014 | Wang | G06K 9/6227 382/133 |
| 2015/0078613 | A1* | 3/2015 | Forutanpour | G06F 3/017 382/103 |
| 2016/0034809 | A1* | 2/2016 | Trenholm | H04L 41/5041 706/20 |
| 2016/0042254 | A1* | 2/2016 | Miyauchi | G06K 9/6256 382/159 |
| 2016/0110584 | A1* | 4/2016 | Remiszewski | G06T 7/0012 382/133 |
| 2017/0109571 | A1* | 4/2017 | McDuff | G06K 9/00302 |
| 2017/0109680 | A1* | 4/2017 | Apte | G06Q 10/06393 |
| 2017/0270346 | A1* | 9/2017 | Ascierto | G06K 9/00147 |
| 2017/0289589 | A1* | 10/2017 | Koumchatzky | G06N 3/0454 |

OTHER PUBLICATIONS

McKenna, S. J., Amaral, T., Akbar, S., Jordan, L., & Thompson, A. (2013). Immunohistochemical analysis of breast tissue microarray images using contextual classifiers. Journal of pathology informatics, 4(Suppl). (Year: 2013).*

Amaral, T., McKenna, S. J., Robertson, K., & Thompson, A. (2013). Classification and immunohistochemical scoring of breast tissue microarray spots. IEEE Transactions on Biomedical Engineering, 60(10), 2806-2814. (Year: 2013).*

Lazebnik, S., Schmid, C., & Ponce, J. (2005). A sparse texture representation using local affine regions. IEEE Transactions on Pattern Analysis and Machine Intelligence, 27(8), 1265-1278. (Year: 2005).*

Tu, Z., & Bai, X. (2010). Auto-context and its application to high-level vision tasks and 3d brain image segmentation. IEEE Transactions on Pattern Analysis and Machine Intelligence, 32(10), 1744-1757. (Year: 2010).*

Amaral et al, Classification and Immunohistochemical Scoring of Breast Tissue Microarray Spots, IEEE Transactions on Biomedical Engineering, Oct. 2013, pp. 2806-2814, vol. 60, No. 10.

Azmi et al, Ensemble Semi-supervised Frame-work for Brain Magnetic Resonance Imaging Tissue Segmentation, Journal of Medical Signals and Sensors, 2013, pp. 94-106, vol. 3, No. 2.

Hean-Ping Chan, Computer-aided classification of mammographic masses and normal tissue: linear discriminant analysis in texture feature space, Phys Med Biol, 1995, 857-876, 40.

International Preliminary Report on Patentability dated Aug. 11, 2016 in corresponding PCT/EP2015/051302 filed Jan. 23, 2015, pp. 1-10.

International Search Report and Written Opnion dated May 15, 2015 in corresponding PCT/EP2015/051302 filed Jan. 23, 2015, pp. 1-14.

Lazebnik et al, Vision Tasks and 3D Brain Image Segmentation, IEEE Transactions on Pattern Analysis and Machine Intelligence, Aug. 2005, pp. 1275-1278, vol. 287, No. 8.

McKenna, S.J., Immunohistochemical analysis of breast tissue microarray images using contextual classifiers, J Pathol Info, 2013, 13, 4.

Rolf Adams, Seeded Region Growing, IEEE Trans Pat Anal Machine Intel, 1994, 641-647, 16.

Tu et al, Auto-Context and Its Application to High-Level Vision Tasks and 3D Brain Image Segmentation, IEEE Transactions on Pattern Analysis and Machine Intelligence, Oct. 2010, pp. 1744-1756, vol. 32, No. 10.

* cited by examiner

Algorithm 1 Adaptive classification

Input: Pre-built training DB $\Theta$, test data $\Gamma$, confidence threshold $\delta_c$.
Output: Classification result, $L = \{l(x_i) \in \mathcal{T} \, \forall x_i \in \Gamma\}$.
1: Build a classifier $\mathcal{F}$ using $\Theta$.
2: Apply $\mathcal{F}$ to each $x_i$, obtain a label $l(x_i)$, and a confidence score $c(x_i) \in [0, 1]$.
3: Find high confidence samples, $\mathbf{x}^h = \{x_i | c(x_i) \geq \delta_c\}$, and low confidence samples $\mathbf{x}^l = \{x_i | c(x_i) < \delta_c\}$. Let $\Delta = \{(x_i, l(x_i)), | x_i \in \mathbf{x}^h\}$
4: Generate an adaptive training DB $\Theta^*$ by combining $\Theta$ and $\Delta$ using Algorithm 2. In Algorithm 2, we consider $\Theta$ as the external training DB, and $\Delta$ as the internal training DB.
5: Learn a classifier $\mathcal{F}^*$ using $\Theta^*$.
6: Use $\mathcal{F}^*$ to re-classify samples in $\mathbf{x}^l$ to obtain $\{l^*(x_i) | x_i \in \mathbf{x}^l\}$.
7: Create $L = \{l(x_i) | x_i \in \mathbf{x}^h\} \cup \{l^*(x_i) | x_i \in \mathbf{x}^l\}$

Fig. 2B

Algorithm 2 Adaptive training database generation
Input: External training DB $\Theta$, internal training DB $\Delta$, tissue type threshold $\delta_t$.
Output: Adaptive training database $\Theta^*$.
1: Let $T(D)(T(D) \subset \mathcal{T})$ denote the list of tissue types represented by a DB $D$, i.e., $\forall t_i \in T(D), \text{card}\{x_i \in D | l(x_i) = t_i\} > \delta_t$ (card: the number of elements in the set). This mean, a tissue type $t_i$ is represented by $D$ if there are sufficent samples of $t_i$ in $D$.
2: Assume that $T(\Theta) = \mathcal{T}$, i.e., the external DB is a complete DB (this means it contains all the tissue types), but $\Delta$ may not be a complete DB. This assumption is motivated from Algorithm 1, where the pre-built training DB is a complete DB, while the high confidence samples obtained from the first classification step may not contain all the tissue types.
3: Create $\Theta^* = \{(x_i, l(x_i)) | (x_i, l(x_i)) \in \Delta \wedge l(x_i) \in T(\Delta)\} \cup \{(x_j, l(x_j)) | (x_j, l(x_j)) \in \Theta \wedge l(x_j) \notin T(\Delta)\}$ (if a tissue type $t_i$ is represented by $\Delta$, we use the samples of $t_i$ in $\Delta$ rather than in $\Theta$, to generate $\Theta^*$).

Fig. 2C

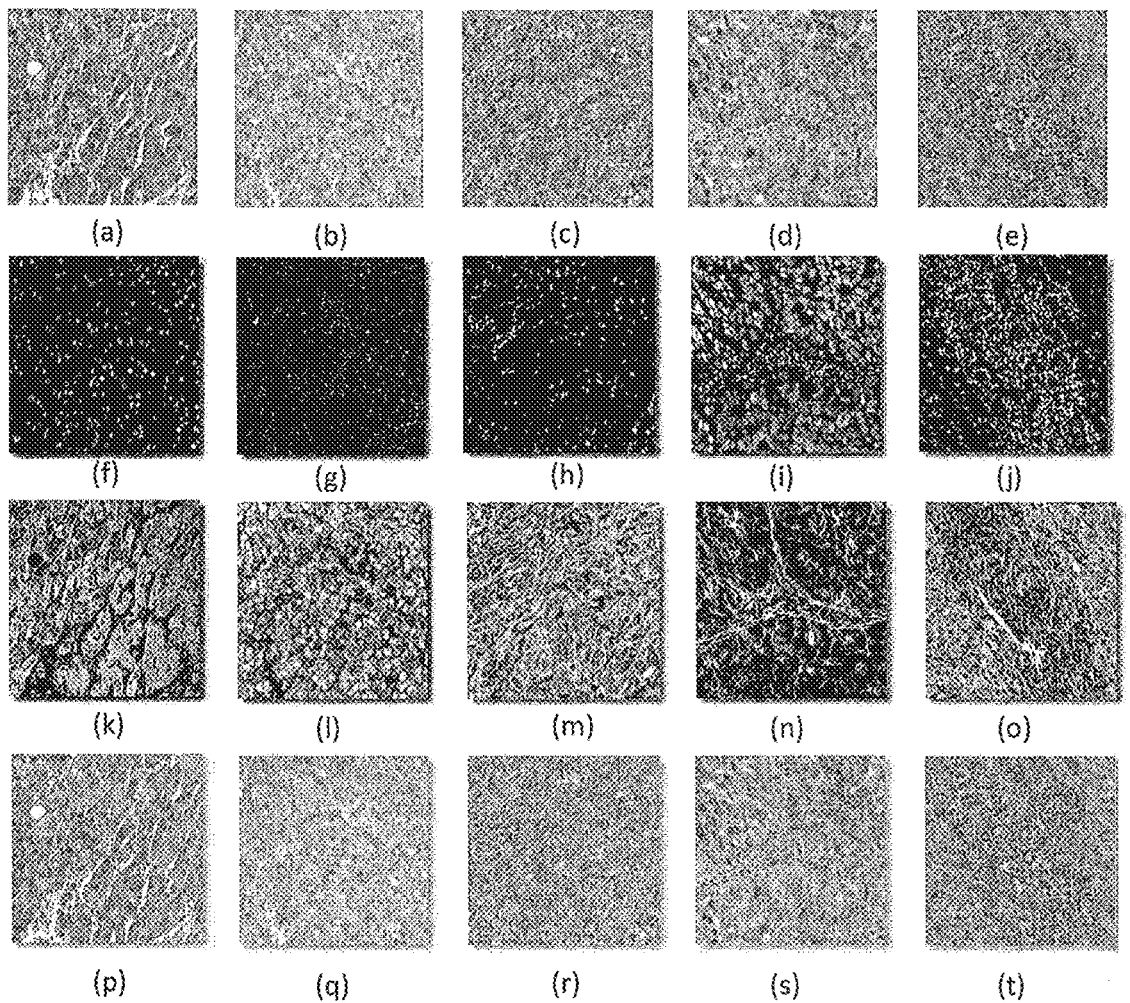
FIGS. 3A-T

FIGS. 5A-D

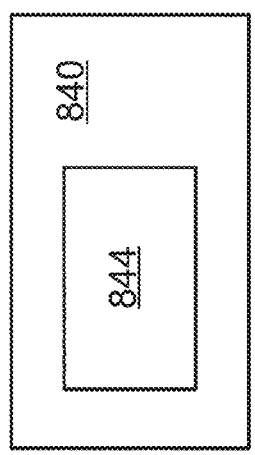
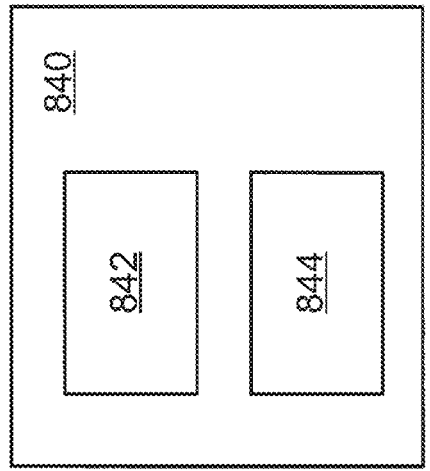
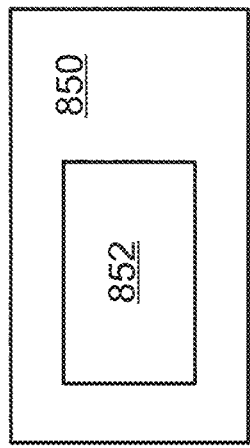
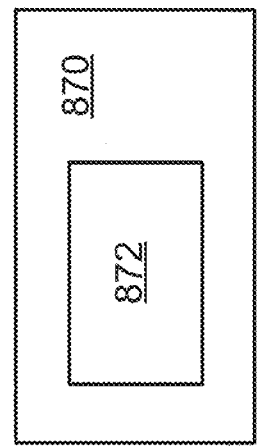
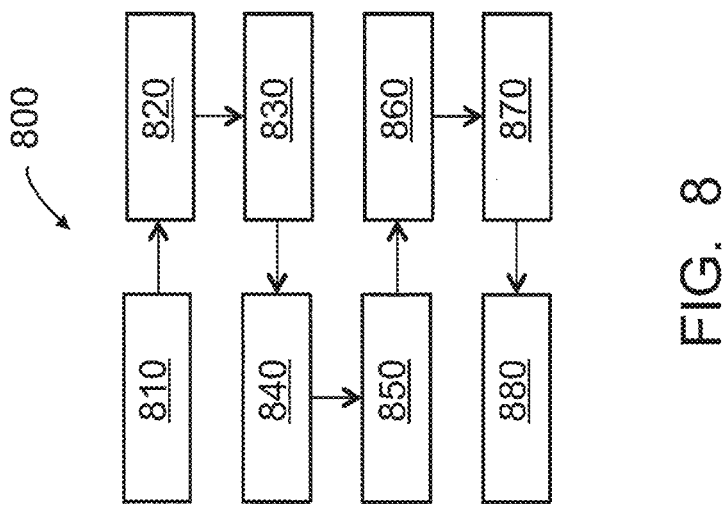

ADAPTIVE CLASSIFICATION FOR WHOLE SLIDE TISSUE SEGMENTATION

CROSS REFERENCE TO RELATED APPLICATIONS

This patent application is a continuation of U.S. patent application Ser. No. 15/222,889 filed Jul. 28, 2016, which is a continuation of International Patent Application No. PCT/EP2015/051302 filed Jan. 23, 2015, which claims priority to and the benefit of U.S. Provisional Patent Application Ser. No. 61/932,671, filed Jan. 28, 2014, and U.S. Provisional Patent Application Ser. No. 62/033,261, filed Aug. 5, 2014. Each patent application listed above is incorporated herein by reference as if set forth in its entirety.

TECHNICAL FIELD

The subject disclosure relates to identifying tissue structures. In particular, the subject disclosure is directed to systems and methods for segmenting an image of tissue

BACKGROUND

Tissue segmentation from histopathology images is an important problem in digital pathology. Given a whole slide (WS) tissue image, many applications require identification of different types of tissue regions in the image, such as normal tissue, tumors, necrosis, lymphocytes, and stroma. The correct identification of these regions may help to provide valuable diagnostic information. For example, a quantitative assessment of the presence of such areas in a sample may be beneficial to determine the impact of a therapy such as chemotherapy. Tissue image segmentation has previously been addressed by various methods. Generally, automatic tissue image segmentation may be achieved by machine learning methods including feature extraction and classification. For example, a small patch may be extracted around each pixel of the image, and various methods may be used to extract features from the patch. Masahiro, I., et al. relates to segmenting stroma in a liver tissue image by segmenting superpixels from the image and identifying lymphocyte density and fiber probability as corresponding to stroma. Ozseven, T., et al. relates to quantifying the necrotic areas on liver tissues using support vector machine (SVM) algorithm and Gabor filters. Doyle, S., et al. discusses a cancer detection method for a prostate tissue image including computing a rich set of textural features such as first-order statistics, co-occurrence, and Gabor features, followed by feature selection using Adaboost to perform pixel classification at different resolutions. Sertel, O., et al. relates to analyzing neuroblastoma histology slides by partitioning the tissue images into stroma-rich, differentiating, poorly-differentiated and undifferentiated regions using co-occurrence features and structural features computed from the Hessian matrix. Nayak, N., et al. relates to applying a dictionary learning method to the tissue segmentation problem. Xu, Y., et al. relates to adopting a multiple instance learning method, also known as weakly supervised learning, for the segmentation of colon tissue images into regions of different cancer types.

However, these methods are inefficient due to the large variation among images and limited training samples. Further, manual annotations of training images are laborious due to large size of the WS image at high magnification and the large volume of data to be processed. Accordingly, the limited segmentation accuracy of prior art methods leaves unmet desires.

SUMMARY

Disclosed herein are systems and methods that address, among other things, the problems identified above using a two-step classification method. Operations disclosed herein include dividing a WS image into a plurality of patches, and first classifying each patch using a "soft" classification, such as SVM, and generating a confidence score and a label for each patch. The location of each patch, its features, its tissue type obtained as classification result, and its confidence score can be stored in a database. The second classification step includes comparing the low-confidence patches with the high-confidence patches in the database and using similar patches to augment the spatial coherence of the patches in the database. In other words, for each low-confidence patch, neighboring high-confidence patches make larger contributions towards refining the labels for each patch, which improves the segmentation accuracy in the low-confidence patches. In contrast to existing adaptive/active learning techniques for growing training databases, the disclosed operations are less concerned with growing a single training database and are instead focused on treating each test image independently while adaptively improving the classification accuracy based on the labeling confidence information for the image under analysis. In other words, a confident label patch database is generated for each image, and similarity retrieval operations are performed within the image to refine the classification results for low-confidence patches.

In one exemplary embodiment, the subject disclosure is a method for segmentation of a tissue image, including identifying grid points in the tissue image, classifying the grid points as one of a plurality of tissue types, and generating classified grid points based on a database of known characteristics of tissue types, assigning the classified grid points at least one of a high confidence score and a low confidence score, modifying the database of known characteristics of tissue types based on the grid points that were assigned a high confidence score, and generating a modified database, and reclassifying the grid points that were assigned a low confidence score based on the modified database. The method may be a computer-implemented method In another exemplary embodiment, the subject disclosure is a digital storage medium to store digitally encoded instructions executable by a processor of an electronic device to perform operations including assigning an image patch of a tissue sample with a tissue type and a confidence score based on a comparison with a database of known features associated with said tissue sample, and refining the tissue type and confidence score for the image patch based on a comparison of the image patch with one or more high-confidence image patches from the same tissue sample, wherein the high-confidence image patches are stored in a database of high-confidence image patches associated with the tissue sample. The electronic device may comprise a single or multi processor data processing system, such as an imaging system, which may support parallel processing.

In yet another exemplary embodiment, the subject disclosure is a system for adaptive classification of a tissue image, the system including a processor; and a memory communicatively coupled to the processor, the memory to store digitally encoded instructions that are executable by the processor to perform operations including classifying a pixel within a tissue image as one of a plurality of tissue types based on a soft classification, and comparing the pixel with one or more neighbor pixels having high confidence scores to refine the classification for the pixel, wherein the high-confidence score of the one or more neighbor pixels is based on the soft classification.

BRIEF DESCRIPTION OF THE DRAWINGS

FIGS. 2A-C illustrate a method for adaptive classification of whole slide images, according to an exemplary embodiment of the subject disclosure.

FIGS. 3A-3T illustrate image channels for 5 different tissue types, according to exemplary embodiments of the subject disclosure.

FIG. 8 schematically shows a flow diagram of an embodiment of a tissue analysis method.

FIG. 8a schematically shows details of step 860 shown in FIG. 8.

FIG. 8b schematically shows details of step 880 shown in FIG. 8.

FIG. 8c schematically shows an embodiment of step 850 shown in FIG. 8.

FIG. 8d schematically shows an embodiment of step 850 shown in FIG. 8.

DETAILED DESCRIPTION

Figure 1:
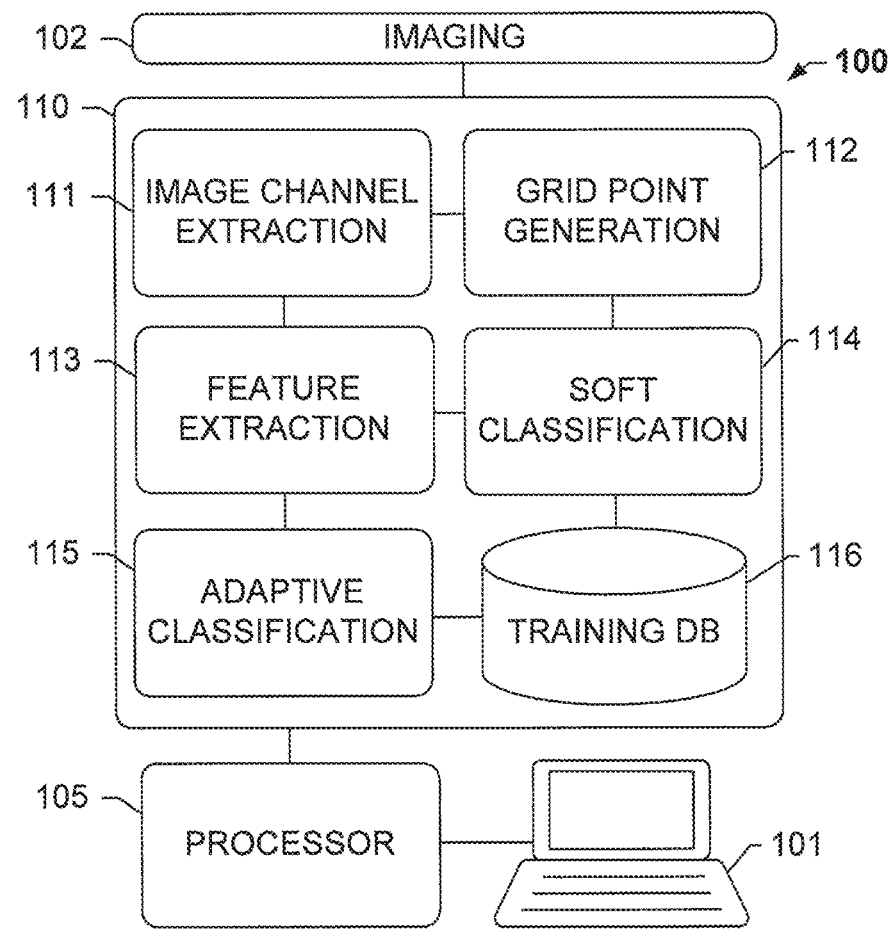
FIG. 1 illustrates a system for adaptive classification of whole slide images, according to an exemplary embodiment of the subject disclosure.

Before elucidating the embodiments shown in the Figures, various embodiments of the present disclosure will first be described in general terms.

The present disclosure relates, inter alia, to an analysis system, e.g. to a tissue analysis system. The system may be suitable for analyzing biological tissue provided on a slide.

The analysis system may comprise an image region identifier module, e.g. an image region identifier module that selects and/or identifies regions of an image of a tissue sample to be analyzed. The selecting/identifying of image regions may be effected as a function of any of a plurality of criteria including, for example, spatial position and/or image content. The defining of image regions may comprise outputting image region data that defines individual image regions, e.g. by specifying the content and/or boundaries of the individual image regions. The selecting of image regions may comprise generating image region data that defines a plurality of subsets of the (received) image data and the defining of image regions may comprise outputting such image region data. The image region identifier module may be or comprise a grid point generation module as described infra.

The image region identifier module may receive image data representative of an image of a tissue sample. The image data may be representative of an at least two-dimensional image, e.g. an at least two-dimensional image of a tissue sample, e.g. on the order of one million to one billion pixels. The image data may comprise a plurality of pixels as known in the art. The image data may represent the image as a grayscale image, a color image (e.g. RGB or CYMK) or a multi-channel image. The multi-channel image may comprise, e.g. as distinct channels of the multi-channel image, image information captured using nonvisible electromagnetic radiation (UV light, for example) or other imaging techniques.

The image region identifier module may receive the image data directly or indirectly from a source that need not be an element of the (tissue) analysis system. In this respect, the (tissue) analysis system may comprise a (tissue) imaging device, e.g. a (tissue) imaging device that images a tissue sample to obtain the image data, such as a multi-channel image, e.g. a multi-channel fluorescent or brightfield image with several (such as between ten to sixteen for example) channels where each channel image is a gray-scale image, of 8 or 16-bit, that corresponds to image capture from a narrow spectral band or a RGB color image with three color channels where each channel is corresponds to the particular color capture. For instance, the source may be a fluorescence microscope, camera, optical, scanner, CCD, or other optical component of an imaging system generating a fluorescent image, or a bright-field microscope, camera, optical scanner, or imaging system generating an RGB image. Examples of imaging systems can be, for example, any fluorescent or a brightfield microscope with spectral filter wheel or a whole slide scanner.

The imaging device may utilize nonvisible electromagnetic radiation (UV light, for example) or other imaging techniques to capture the image. The (tissue) imaging device may comprise a microscope and a camera arranged to capture images (of tissue) magnified by the microscope. The image data received by the image region identifier module may be identical to and/or derived from raw image data captured by the (tissue) imaging device.

The image region identifier module may generate and/or output image region data that identifies a plurality of subsets of the (received) image data. Any individual subset of the image data subsets may be representative of a respective region of the image. The image region data may identify the respective subsets by grouping of the image data, e.g. into data structures representative of the respective subsets. For example, the image region data may comprise a plurality of (subset) data structures, each (subset) data structure comprising the image data of a single (respective) subset. As such, the image region identifier module may generate at least one such (subset) data structure. Similarly, the image region data may identify the respective subsets by designating boundaries that define which image data (e.g. pixels of the image data) belong to the respective subset. As such, the image region identifier module may generate image region data designating such boundaries. For example, the image region identifier module may generate data that identifies a plurality of pixels of the image data as grid points and data representative of a geometry, the geometry defining individual regions, i.e. subsets, of the image data relative to the respective grid points. As such, each of the terms "grid point" and "data image subset" may be understood as designating a region of the image, i.e. a point/pixel in the image and a neighborhood around that point. As such, each of the terms "grid point" and "data image subset" may designate a set of pixels of the image, e.g. a set of pixels representative of a region of the tissue sample.

Any of the regions may be a spatially contiguous region, e.g. a point/pixel in the image and a spatially contiguous neighborhood around that point. As such, the term "region" may designate a spatially contiguous set of pixels of the image, e.g. a set of pixels representative of a spatially contiguous region of the tissue sample.

The individual regions (represented by the respective image data subsets) may be of various sizes or shapes. For example, a region may be square, rectangular, hexagonal or circular. Similarly, a region may be as small as a single pixel or have a diameter of several tens/hundreds of pixels. For example, the individual regions may be squares on the order of 100×100 pixels. As such, the grid points may be located at regular intervals in at least one dimension. For example, the grid points may be located at the cross points of a square or rectangular (two-dimensional) grid. Similarly, the regions may be arranged in a honeycomb-like arrangement. As such, the grid points may be arranged in the general form of an array, the grid points of alternate rows of the array being offset, in the row direction, from the grid points in the other alternate rows by half of the spacing of the grid points in the row direction. The image region identifier module may select the respective image regions using user-defined region sizes, grid point spacings, region shapes/geometries, grid point arrays, grid point/region arrangements, region overlap limits, etc. (as selection parameters). The user interaction underlying such user-defined parameters may be effected by the analysis system or by another system. As such, the user-defined parameters may be received by the analysis system over a network or from a data storage device.

The individual regions (represented by the respective image data subsets) may be unique, i.e. not identical to another region. The individual regions may overlap or may be without overlap. For example, the individual regions may be arranged/shaped such that not more than 30%, not more than 20%, not more than 10% or 0% of the area of a respective individual regions overlaps other regions. As such, the subsets of image data need not be mutually exclusive. In other words, any one of the plurality of subsets of image data may comprise image data belonging to another subset of the plurality of subsets of image data.

The analysis system may comprise an image region classifier module, e.g. an image region classifier module that classifies any image region of the image regions as one of a plurality of tissue types. For example, the image region classifier module may individually classify any individual image region of the image regions as a respective one of a plurality of tissue types. The image region classifier module may individually classify each individual image region of the image regions. The image region classifier module may comprise a memory that stores the plurality of tissue types (available as a possible classification for the image regions). The plurality of tissue types may comprise any of normal tissue, tumor, necrosis, stroma, and lymphocyte aggregates. The image region classifier module may classify several thousand or several ten thousand of the image regions, e.g. at least five thousand, at least ten thousand or at least twenty thousand of the image regions.

The image region classifier module may classify the respective image region using the image data subset representative of the respective image region. For example, the image region classifier module may classify the respective image region by performing image processing on pixels belonging to the respective image data subset. The image region classifier module may classify the respective image region using the respective image data subset for querying a database, e.g. a database of tissue characteristics. For example, the image region classifier module may derive features of the respective image region from the respective image data subset and use the derived features to query the database. Furthermore, the image region classifier module may classify the respective image region using data obtained from a database, e.g. a database of tissue characteristics. For example, the image region classifier module may use data obtained from the database to train a machine learning algorithm (for classifying individual image regions) and may process the respective image data subset by means of the machine learning algorithm trained using the data obtained from the database (to classify the tissue type of the respective image region). Similarly, the image region classifier module may classify the respective image region by comparing data obtained from the database with pixel information of pixels belonging to the respective image data subset and/or with results of an image processing on pixels belonging to the respective image data subset. The data obtained from the database may be representative of an image, image features, a classification ascribed to particular image information and/or a classification ascribed to a particular set of image features. As such, the data obtained from the database may comprise a pairing of classification information and image information and/or a pairing of classification information and information representative of at least one image feature. The image region classifier module may be or comprise a soft classification module as described infra.

The image region classifier module may determine and/or output a confidence score, e.g. a confidence score indicative of the confidence of the classifying of a respective image region. As such, any classifying of an individual image region may have a respective confidence score, and any confidence score may relate to the classifying of a respective, individual image region. The confidence score may be representative of a probability that the classifying of the respective image region is correct, i.e. confidence score "1". The image region classifier module may determine the confidence score by determining a degree of similarity between pixels belonging to the respective image data subset to image information obtained from the database and/or by determining a degree of similarity between results of an image processing performed on pixels belonging to the respective image data subset and image feature information obtained from the database. The outputting of a confidence score may comprise outputting data representative of the confidence score.

The analysis system may comprise a database modifier module. The database modifier module may effect modification of the database, e.g. by issuing instructions directly or indirectly to the database that result in an execution of (database) operations that modify the database. For example, the database modifier module may issue instructions to the database that result in an addition/modification/deletion of data to/in/from the database.

The database modifier module may effect modification of the database for any of the image regions, e.g. for any of the image regions classified by the image region classifier module. For example, the database modifier module may effect modification of the database for any image region having a confidence score falling within a first range. In other words, the database modifier module may effect modification of the database for any image region whose classifying by the image region classifier module has a confidence score falling within the first range. The first range may be a range of confidence scores that includes a confidence score representative of certainty that the classification is correct. As such, the database may effect modification of the database in response to a classifying of an image region, which classifying is sufficiently probable of being correct, i.e. has a confidence score falling within the first range. The image region classifier module may effect modification of the database for several hundred or several thousand of the image regions (having a confidence score falling within a first range), e.g. at least five hundred, at least one thousand, at least five thousand or at least ten thousand of the image regions (having a confidence score falling within a first range).

The database modifier module may effect modification using the tissue type classified to the respective image region. Similarly, the database modifier module may effect modification using the confidence score relating to the classifying of the respective image region. Furthermore, the database modifier module may effect modification using the respective image data subset, e.g. using pixels belonging to the respective image data subset, information pertaining to a location of the respective image region relative to other image regions, results of an image processing performed on pixels belonging to the respective image data subset and/or (other) tissue characteristic data obtained from the respective image data subset. As such, the database modifier module may effect modification such that the resultant modified database comprises data representative of the tissue type classified to the respective image region and tissue characteristic data obtained from the respective image data subset.

The analysis system may comprise an image region reclassifier module, e.g. an image region reclassifier module that reclassifies any image region of the image regions as one of the plurality of tissue types. For example, the image region reclassifier module may individually reclassify any individual image region of the image regions as a respective one of the plurality of tissue types. The image region reclassifier module may comprise a memory that stores the plurality of tissue types (available as a possible reclassification for the image regions). As stated above, the plurality of tissue types may comprise any of normal tissue, tumor, necrosis, stroma, and lymphocyte aggregates. The image region reclassifier may, for any of the image regions, output the tissue type determined by the reclassifying of the respective image region. The outputting of the tissue type may comprise outputting data representative of the tissue type and/or outputting an instruction that effects further modification of the modified database to include the tissue type and/or data representative of the tissue type, e.g. in conjunction with other data pertaining to the respective image region such as image data, a confidence score representative of certainty that the reclassification is correct and/or (tissue) features.

The image region reclassifier module may reclassify any image region having a confidence score falling within a second range. For example, the image region reclassifier module may individually reclassify each image region having a confidence score falling within the second range. The second range may be a range of confidence scores that includes a confidence score representative of certainty that the classification is incorrect, i.e. confidence score "0" or above. As such, the image region reclassifier module may reclassify an image region in response to a classifying of that image region, which classifying is sufficiently probable of being incorrect, i.e. has a confidence score falling within the second range. The image region reclassifier module may be or comprise an adaptive classification module as described infra.

The image region reclassifier module may reclassify the respective image region using the image data subset representative of the respective image region. For example, the image region reclassifier module may reclassify the respective image region by performing image processing on pixels belonging to the respective image data subset. The image region reclassifier module may reclassify the respective image region using the respective image data subset for querying the modified database (of tissue characteristics). For example, the image region reclassifier module may derive features of the respective image region from the respective image data subset and use the derived features to query the modified database. Furthermore, the image region reclassifier module may reclassify the respective image region using data obtained from the modified database, e.g. the database of tissue characteristics modified as discussed above. For example, the image region reclassifier module may use data obtained from the modified database to (re)train a machine learning algorithm (for reclassifying individual image regions) and may process the respective image data subset by means of the machine learning algorithm (re)trained using the data obtained from the modified database (to reclassify the tissue type of the respective image region). Similarly, the image region reclassifier module may reclassify the respective image region by comparing data obtained from the modified database with pixel information of pixels belonging to the respective image data subset and/or with results of an image processing on pixels belonging to the respective image data subset. The data obtained from the modified database may be representative of an image, image features, a classification ascribed to particular image information and/or a classification ascribed to a particular set of image features. As such, the data obtained from the modified database may comprise a pairing of classification information and image information and/or a pairing of classification information and information representative of at least one image feature.

The analysis system may comprise a data storage system that stores the database. The database may comprise, for each of a plurality of tissue image regions, any of data representative of an at least two-dimensional image of tissue, data representative of at least one tissue feature, data representative of a tissue type and data representative of a confidence score. The data representative of at least one tissue feature stored for any respective image region may be data derived from the tissue image stored for the respective image region. Similarly, the confidence score represented by the data stored for any respective image region may be the confidence score for the classifying via which the tissue type represented by the data stored for the respective image region was determined. Furthermore, the tissue image represented by data stored for any respective image region may be a tissue image used for a classifying of the respective tissue image region, which classifying yielded the tissue type represented by the data stored for the respective image region.

The analysis system may comprise a support vector machine, e.g. a support vector machine as described hereinbelow. The support vector machine may be an element of the image region (re)classifier module. The analysis system/image region (re)classifier module may use the support vector machine to determine the confidence score (of a (re)classifying of a respective image region). In other words, the determining of a confidence score may comprise executing one or more support vector machine operations.

The (re)classifying of any respective image region may comprise extracting at least one feature from the respective image region, e.g. by means of a feature extraction module as described infra. The extracting may be effected using the respective image data subset, e.g. using pixel information for the respective image region. Similarly, the extracting may be effected using data obtained from the database (or a modified version thereof), e.g. using data stored in the database pertaining to other image regions as described above. The extracting may be effected by comparing pixel information for the respective image region and/or data derived from such pixel information with the data obtained from the database, e.g. with respectively corresponding types of data obtained from the database. The extracting may extract features belonging to the group consisting of textural features, biological features, intensity features, gradient features, Gabor features, co-occurrence features, and nuclei features.

The reclassifying of any respective image region may comprise weighting data of the respective image data subset and/or the data obtained from the modified database. The weighting may be effected using at least one of a spatial proximity value, a confidence score and feature similarity value. For example, the weighting may comprise weighting classifications obtained from the database as a function of the spatial proximity (on the sample/in the image) of the image region in the database to which the respective classification pertains and the respective image region being reclassified. Similarly, the weighting may comprise weighting image features obtained from the database as a function of a confidence score stored in the database with respect to a tissue type classification of the image region to which the respective image features pertains. Furthermore, the weighting may comprise weighting a set of image features obtained from the database as a function of their respective similarity to a set of image features in the respective image region being reclassified. A feature similarity value indicative of the similarity of one set of image features to another set of image features may be determined as a function of the similarity of the spatial relationship of the individual features within the one set to the spatial relationship of the individual features within the other set and/or as a function of the similarity of the number of individual features of a certain type within the one set to the number of individual features of the certain type within the other set.

The analysis system may comprise an image channel extractor, e.g. an image channel extraction module as described infra. The image channel extractor may be an element of the image region (re)classifier module.

The classifying of a respective image region may comprises separating, e.g. using the image channel extractor, at least the respective region of the image into one or more component channels, for example into one or more component channels belonging to the group consisting of a hematoxylin channel, an eosin channel and a luminance channel. Similarly, the separating may comprise separating any image region, e.g. the entire image, into one or more (of the aforementioned) component channels. The separating may be performed prior to the aforementioned extracting (of features). The extracting (of at least one feature from a respective image region) may be effected using any of the component channels of the respective image region.

The present disclosure relates, inter alia, to an analysis method, e.g. to a tissue analysis method. The method may be suitable for analyzing biological tissue provided on a slide. As such, the aforementioned discussion of an analysis system applies mutatis mutandis, to an analysis method employing the techniques described above.

The various embodiments of the present disclosure having been described above in general terms, the embodiments shown in the Figures will now be elucidated.

FIG. 1A illustrates a system 100 for adaptive classification, according to an exemplary embodiment of the subject disclosure. System 100 comprises a memory 110, which stores a plurality of processing modules or logical instructions that are executed by processor 105 coupled to electronic processing device 101. A "module" as understood herein encompasses a software or hardware module or a combination of software and hardware that provides the respective functionality. Besides processor 105 and memory 110, electronic processing device 101 also includes user input and output devices such as a keyboard, mouse, stylus, and a display/touchscreen. As will be explained in the following discussion, processor 105 executes logical instructions stored on memory 110, performing image analysis and other quantitative operations resulting in an output of results to a user operating electronic processing device 101 or via a network.

For instance, imaging system 102 may provide image data from one or more scanned slides to memory 110. The image data may include an image, as well as any information related to an imaging platform on which the image was generated. For instance, a tissue section may need to be stained by means of application of a staining assay containing one or more different biomarkers associated with chromogenic stains for brightfield imaging or fluorophores for fluorescence imaging. Staining assays can use chromogenic stains for brightfield imaging, organic fluorophores, quantum dots, or organic fluorophores together with quantum dots for fluorescence imaging, or any other combination of stains, biomarkers, and viewing or imaging devices. Moreover, a typical section is processed in an automated staining/assay platform that applies a staining assay to the section, resulting in a stained sample. There are a variety of commercial products on the market suitable for use as the staining/assay platform, one example being the VENTANA SYMPHONY product of the assignee Ventana Medical Systems, Inc. Stained tissue may be supplied to an imaging system, for example on a microscope or a whole-slide scanner having a microscope and/or imaging components, one example being the VENTANA iScan Coreo product of the assignee Ventana Medical Systems, Inc. Multiplex tissue slides may be scanned on an equivalent multiplexed slide scanner system. Additional information provided by imaging system 102 may include any information related to the staining platform, including a concentration of chemicals used in staining, a reaction times for chemicals applied to the tissue in staining, and/or pre-analytic conditions of the tissue, such as a tissue age, a fixation method, a duration, how the section was embedded, cut, etc.

Moreover, although the embodiments described herein refer to Hematoxylin and Eosin (H&E) stained sections from colorectal cancer metastases in liver imaged on a brightfield whole slide (WS) scanner that creates RGB images, the subject disclosure is applicable to any type of image of any biological specimen or tissue. The image may be generated from a whole or a part of a biological specimen positioned on a substrate, such as a slide, or not. The subject disclosure is further applicable to any image type, including RGB, brightfield, darkfield, and fluorescent images.

Image channel extraction module 111 may be executed to facilitate feature extraction and classification by separating the input image into different image channels. For example, separate channels representing the local amounts of Hematoxylin, the local amount of Eosin, and luminance may be generated by image channel generation module 111. For example, a color deconvolution or unmixing method such as the method described in Ruifrok, A. and Johnston, D., "*Quantification of histochemical staining by color deconvolution*," Analyt. Quant. Cytol. Histol. 23, 291-299 (2001) is applied to decompose the original RGB image into Hematoxylin (HTX) and Eosin channels. Further, the luminance channel (the L component of the Lab color space) of the image may also be identified. These channels highlight different tissue structures in the tissue image, thus, they may be referred to as structural image channels. More precisely, the HTX channel highlights nuclei regions (see grey regions in FIG. 2A), the eosin channel highlights eosinophilic structures (dark regions in FIG. 2A), while the luminance channel highlights fatty structures, lumen and spaces (light regions in FIG. 2A). Therefore, features extracted from these channels are useful in describing the tissue structures. The selection of structural image channels can be adjusted for each segmentation problem. For example, for IHC stained images, structural image channels can include the counterstain channel, one or more immunohistochemistry-stained channels, hue, and luminance, as further depicted in FIGS. 3A-T.

Grid point generation module 112 may be executed to divide the WS image into a plurality of patches by sampling a uniform grid of seed points in the image and specifying an interval or neighborhood for each seed point. For example, a grid of points (GPs) with an interval of d=80 pixels may be overlaid on the WS image, enabling feature extraction module 113 to extract features from the neighborhood of these GPs and classification modules 114 and 115 to classify the features and therefore GPs into different tissue types. The interval size is not limited to 80 pixels, and may vary. Further, the grid may be in any shape, such as square, rectangular, hexagonal, etc.

Feature extraction module 113 performs feature extraction on one or more of the image channels. For each GP associated with each image channel, feature extraction module 113 extracts image features in the neighborhood of these points, and different types of image features are extracted, including texture features and biological features. For example, given a neighborhood size s, and image channel c, let $\Omega_{s,c}$ denote a neighborhood of size s×s, at channel c, from which features are extracted. Features computed for all $\Omega_{s,c} \forall S$, c∈C (where S, C denote the sets of selected neighborhood sizes, and selected channels, respectively) are concatenated to generate a feature vector containing rich information to represent the GP. In one experimental embodiment, for instance, S=[100; 200] pixels and C={HTX, Eosin, Luminance}. Moreover, while texture features are computed for all image channels, biological features are computed only for those image channels were the biological structure is present. For example, features for cell nuclei are extracted from the Hematoxylin channel where nuclei regions are salient. A feature selection method is applied on the pool of training features to select a subset of good features for classification. For example, structures in nuclei-rich areas, e.g., tumor and lymphocyte aggregates (LAs), have most signal in the HTX channel, whereas normal liver, necrosis, and stroma have most signal in the Eosin channel. See FIGS. 3A-T for additional details regarding these structures. To capture this difference, intensity-based features including a 10-bin histogram may be computed, and used as features together with mean and variance of pixel intensities in each s, c. For other applications, in addition or instead of a 10-bin histogram, mean, and variance, other descriptive statistics values like a histogram with more or less bins, mean, standard deviation, kurtosis, different percentiles, etc. may be computed. The size of the bin and type of bin may vary. In one experimental embodiment disclosed herein, the total number of features is 12×2×3=72. Among tissues that stain strongly with Eosin (also called eosinophilic tissues), normal liver usually contains large homogeneous cell groups with similarly oriented edges in the Eosin and luminance channels, strong intensity variation and disorganized structures with randomly-oriented edges for necrosis, ridge-like structures for stroma, and other variations as shown in further detail in FIGS. 3A-T. To leverage these textural differences, feature extraction module 113 may extract gradient, Gabor, co-occurrence, and nuclei features for each of the three image channels.

Various types of feature extraction are listed herein. For gradient extraction, feature extraction module 113 may first compute the gradient magnitude and gradient orientation of the image. The gradient features include a 10-bin histogram of gradient magnitude, and a 10-bin histogram of the gradient vector orientation. These features differentiate homogeneous from inhomogeneous regions, and differentiate regions with similarly oriented edges from regions with randomly oriented edges. Again, in addition to a histogram, different descriptive statistics like mean, standard deviation, kurtosis, percentiles etc. can be used as features of the gradient magnitude and orientation. In an experimental example, the total number of features is 20×2×3=120. For Gabor features, feature extraction module 113 may generate 18 Gabor filters [see Jain, A. K., Farrokhnia, F.: Unsupervised texture segmentation using Gabor filters. In: IEEE Int. Conf. Sys., Man., Cyber., pp. 14-19 (1990)] using three different wavelengths and six different orientations. The mean and variance of the filter responses are used as the features. The number of wavelengths, orientations, and the descriptive statistics that are used as features can be selected for each application. In an experimental example, the total number of features is 36×2×3=216. For co-occurrence features, feature extraction module 113 may compute the co-occurrence matrix (CM) of pixel intensity, and compute 13 Haralick features from this CM [see Haralick, R., et al.: Textural Features for Image Classification. IEEE Trans. Sys., Man., Cyber. 3 (6), 610-621 (1973)], including energy, correlation, inertia, entropy, inverse difference moment, sum average, sum variance, sum entropy, difference average, difference variance, difference entropy, and two information measures of correlation. In addition to the conventional gray-level CM (GLCM), which may be computed for each channel individually, the inter-channel or color co-occurrence matrix (CCM) may additionally be used. The CCM is created from the co-occurrence of pixel intensities in two different image channels, i.e., to compute the CCM from two channels Ci;Cj using a displacement vector d=[dx; dy], the co-occurrence of the pixel intensity is computed at location (x; y) in Ci and the pixel intensity at location (x+dx; y+dy) in Cj. The advantage of the CCM is that it captures the spatial relationship between different tissue structures (highlighted in different channels), without the need of explicitly segmenting them. Further, Haralick features may be computed from the GLCMs of all three channels, and Haralick features computed from the CCMs of all pairs of channels (HTX-Eosin, HTX-Luminance and Eosin-Luminance). In an experimental embodiment, the total number of features may be 13×2×(3+3)=156. Further, nuclei features may be extracted using density, shape, size, and appearance of cell nuclei to provide strong features to distinguish tissue types using, for instance, the methods described in Masahiro, I., et al.: Automatic segmentation of hepatocellular structure from HE-stained liver tissue. In: Proc. SPIE, pp. 867611-867611-7 (2013)]. Although texture features computed from the HTX channel capture a certain amount of nuclei information, explicit nuclei-related features may be additionally computed. For instance, the system may first detect nucleus centers from the HTX channel (where nuclei are most salient) using a radial-symmetry-based method [Parvin, B., et al.: Iterative voting for inference of structural saliency and characterization of subcellular events. IEEE Trans. Image Processing 16(3), 615-623 (2007)], followed by segmenting nuclei regions by Otsu's method [Otsu, N.: A threshold selection method from gray-level histograms. IEEE Trans. Sys., Man., Cyber. 9(1), 62-66 (1979)]. Since the pixel intensity in the nuclei regions varies, the Otsu method may be applied on a local neighborhood of each detected nuclei center. Based on the segmentation result, the system may compute: (i). nuclei density (the number of detected nuclei), (ii) nuclei size (average of the nuclei areas), and (iii) average intensity value in the nuclei regions. In summary, a total of 72+120+216+156+3=567 features may be created to form the feature vector for each GP. These nucleus-related features are one example for biological features that capture the occurrence, density, and properties of biologic objects, like nuclei, cells, glands etc. in the tissue that are detected to create features for classification.

Subsequent to feature extraction, the two-stage classification is performed in order to efficiently and robustly process variability in tissue appearance. First, a soft classification module 114 may be executed to classify each patch using a "soft" classification, such as SVM, and generating a confidence score and a label for each patch. This soft classification includes classifying all GPs in a WS image $W_i$ using an external (pre-built) training database comprising known features, and generating a label and a confidence score for each GP. For example, an output label of the SVM for a particular region type such as a tumor region may be a scalar value from 0 to 1, where 0 indicates no possibility of the region being a tumor, and 1 indicates a high likelihood that the GP belongs to a tumor region. A confidence map may be generated for the patches in the image using the confidence determinations for each GP. The highest confidence GPs from $W_i$ may be added to an internal training database that is combined with the external database to generate an adaptive training DB for $W_i$. For example, confidence scores of >0.8 may be considered as high confidence GPs and may be added to the database. Training database 116 may include the combined database. In other embodiments, the external training database for soft classification may be incorporated within training database 116. Database 116 may also store confidence and labels for patches for each image.

Adaptive classification module 115 is executed to perform the second classification step, including comparing the low-confidence patches with the high-confidence patches in training database 116, and using similar patches to augment the spatial coherence of the patches in the database. Based on the tissue features of a low-confidence patch, similarity retrieval operations are performed within the image to refine the classification results for low-confidence patches. In other words, for each low-confidence patch, neighboring high-confidence patches make larger contributions towards refining the labels for each patch, which improves the segmentation accuracy in the low-confidence patches. For example the top 10 similar patches may be obtained, and the majority label from them used as the new label for a low confidence patch or pixel. Therefore, the adaptive database stored in database 116 enables re-classifying the low confidence patches in W. The spatial restraints around the low-confidence patches enable providing more weights to high-confidence patches and low weights to similar patches that are further away from the low-confidence patches.

Due to high resolution and large number of pixels in each image, the resulting database-per-image may be quite comprehensive. The large variation across different images enables the disclosed systems and methods to adaptively improve the segmentation results based on the patterns in each image. In exemplary embodiments of the subject disclosure, biological information relevant to image data, for example, data collected or obtained in accordance with the methods disclosed herein, is utilized to design specific features to train database 116 for the specific image. The similarity retrieval works well for features within the same image, enabling improvement of segmentation accuracy in the low-confidence regions. Moreover, a refined confidence map may be generated for the patches in the image using the $2^{nd}$ step confidence determinations for each GP. The confidence map and the map of tissue types may be output to a user operating terminal 101, or transmitted across a network to a remote terminal. The confidence map and the map of tissue types may be electronically analyzed to determine a quality of the image, or to obtain a diagnosis for treatment or a prognosis for a patient.

As discussed herein, various different classification methods can be applied to the detected features. In exemplary embodiments, these different methods may be evaluated and a random forest classification method may be chosen due to superior performance. In an experimental embodiment disclosed herein, performance was evaluated with a database including more than 84,000 seeds of five different tissue types: liver, CRC metastasis, lymphocyte, necrosis and stroma (the ground truth was provided by a pathologist). These five tissue types are examples of tissue type classifications, and the disclosed systems and methods are not limited to these five tissue types. The tissue types may vary for different types of tissue, for example, when the tissue image is not a liver tissue image. The seed classification accuracy obtained was 89%. Moreover, image segmentation results are also obtained for 27 whole slide tissue images. The experimental results demonstrate the usefulness of the machine-assisted diagnosis system. In an experimental embodiment, the segmentation may be performed using the conventional supervised framework similar to the work in Ozseven, T., et al.: Quantifying the necrotic areas on liver tissues using support vector machine (SVM) algorithm and Gabor filters.

Figure 2A:
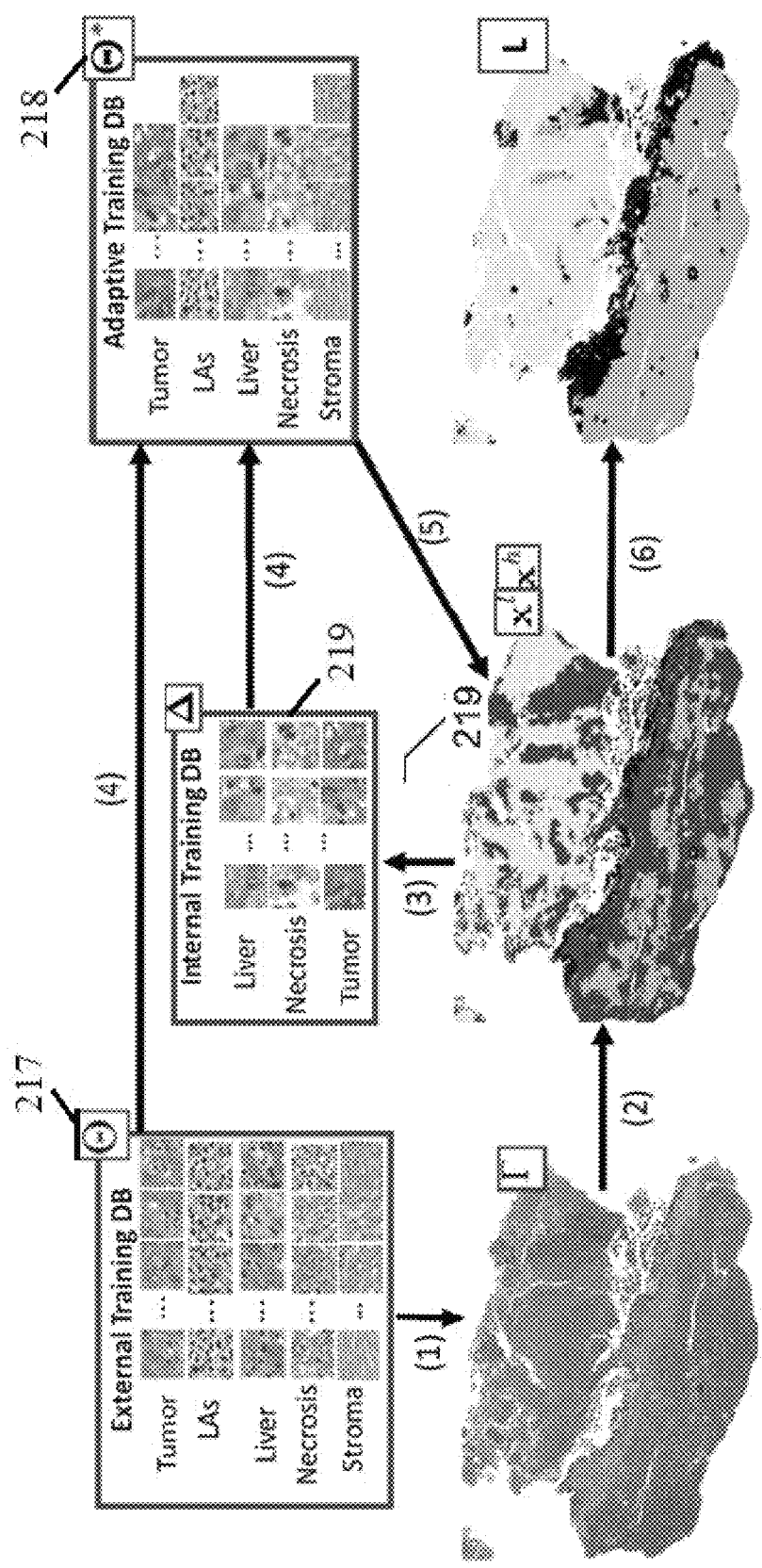

FIGS. 2A-2C show a method for adaptive classification, according to an exemplary embodiment of the subject disclosure. To leverage or utilize the large size of a WS image (i.e., the large amount of GPs being generated per slide), the two-stage classification procedure includes a first stage wherein a pre-built training first database (DB) Θ 217 is used to classify all GPs in the image (steps (1), (2), (3)). Next, the GPs with high classification confidence are considered as a new second training DB (219), which is combined with Θ 217 to create an adaptive training modified DB Θ* 218 (step (4)). Based on the assumption that the classification accuracy is higher when the training data belong to the same WS image as the data that has to be classified, Θ* 218 provides appropriate data to re-classify (step (5)) the GPs that were classified with low confidence when using Θ. Since Θ* 218 is built adaptively for each WS image, the method is referred to as adaptive classification. Depending on the implementation, the modified DB Θ* 218 may replace the pre-built training first database (DB) Θ 217 for a subsequent image (e.g. an image taken from the same slide or another slide of a tissue sample obtained from the same patient) that needs to be analysed such that the pre-built training first database is gradually improved. In this method, T={normal liver, tumor, necrosis, LAs, stroma} may be defined as the list of all tissue types of interest. The confidence scores for the test samples in Algorithm 1 (FIG. 2B) may be obtained using the distances to the decision boundary in the SVM, the voting scores generated by random forest, or the percentage of labels of the nearest neighbors in k-nearest neighbors classifiers. Algorithm 1 refers to Algorithm 2 (depicted in FIG. 2C). It is to be noted that in the embodiments of FIGS. 2B and 2C the "confidence threshold $\delta_c$" divides the confidence range between 0 to 1 into the first and second ranges between 6, and 1 and between 0 and $\delta_c$, respectively. The "test data Γ'" are the image data subsets to be classified.

FIG. 3 illustrates five (5) tissue types, according to an exemplary embodiment of the subject disclosure. FIGS. 3A, 3B, 3C, 3D, and 3E respectively depict scans of H&E stained from colorectal cancer metastases from normal liver, necrosis, stroma (peritumoral stroma), tumor, and lymphocyte aggregates (LA) sections. FIGS. 3F-3J depict the HTX structural image channel corresponding to each of these tissue types, FIGS. 3K-O depict the Eosin structural image channel, and 3P-3T depict the luminance structural image channel. Each of these channels highlights different tissue structures in the tissue image, thus, they are referred to as structural image channels. Tumor tissue may sometimes contain intratumoral stroma (in FIG. 3D, which is salient in FIG. 3N), however, the tissue may still be considered as a solid tumor.

As mentioned herein, structures in nuclei-rich areas (e.g., tumor and LAs) may have the most signal in the HTX channel (FIGS. 3F-3J), whereas normal liver, necrosis, and stroma have most signal in the Eosin channel (FIGS. 3K-3O). To capture this difference, intensity-based features including a 10-bin histogram may be computed, and used as features together with mean and variance of pixel intensities in each s, c. For other applications, in addition or instead of a 10-bin histogram, mean, and variance, other descriptive statistics values like a histogram with more or less bins, mean, standard deviation, kurtosis, different percentiles, etc. may be computed. The size of the bin and type of bin may vary. In one experimental embodiment disclosed herein, the total number of features is 12×2×3=72. Among eosinophilic tissues, normal liver usually contains large homogeneous cell groups with similarly oriented edges in the Eosin and Luminance channels (FIGS. 3K and 3P). In contrast, for necrosis, these channels contain strong intensity variation and disorganized structures with randomly-oriented edges (FIGS. 3L and 3Q). Finally, in stroma, these channels contain more ridge-like structures (FIGS. 3M and 3R). For basophilic tissues, tumor typically contains larger nuclei, with lower pixel intensity in the nuclei region in the HTX channel than LAs (FIGS. 3I and 3J).

Figure 4:
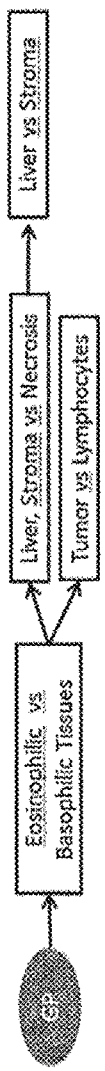
FIG. 4 illustrates a hierarchical strategy for multi-class GP segmentation, according to an exemplary embodiment of the subject disclosure.

In an experimental embodiment, the dataset used to evaluate the proposed method included 27 slides of liver samples with metastases from colorectal cancer, digitized at 20× magnification on a Ventana iScan HT whole-slide scanner (0.465 μm/pixel), with an average size of 26,600× 22,800 pixels. In each of the 27 images, a number of GPs are selected and assigned to five tissue types by expert observers, resulting in a GP dataset of more than 84,000 labeled GPs in total. In a first part of the experiment, conventional training and classification procedures were performed on the GP dataset without the adaptive classification procedure. The purpose is to validate the discriminative power of the extracted features. The GP dataset is divided into three groups, two for training and one for validation. To avoid overfitting, data are divided such that GPs from the same image are not present in both the training and test data at the same time. The process is repeated three times, each with different training and validation groups, and the average classification accuracy is reported. The performance of different classifiers is compared, namely k-nearest neighbors (kNN), support vector machine (SVM), and random forest (RF). Moreover, due to the high dimensionality of the feature space, principal component analysis (PCA) and min redundancy-max relevance (mRMR) [Peng, H., et al.: Feature selection based on mutual information: criteria of max-dependency, max-relevance, and min-redundancy. IEEE Trans. Pattern Analysis and Machine Intelligence 27(8), 1226-1238 (2005)] are considered for dimensionality reduction, in competition against the full feature set. The multi-class classification problem is solved by combining multiple binary classification problems, using two strategies, namely one-vs-one and hierarchical. See FIG. 4 for an illustration of a hierarchical strategy for multi-class GP segmentation, according to an exemplary embodiment of the subject disclosure.

Table 1 summarizes all the classification accuracies (%) with standard deviation for different selections of classifiers, dimensionality reduction methods, and multi-class classification strategies.

TABLE 1

| | One-vs-one strategy | | | Hierarchical strategy | | |
|---|---|---|---|---|---|---|
| Classifier | Full features | mRMR | PCA | Full features | mRMR | PCA |
| SVM | 87.7 (2.5) | 87.4 (1.8) | 87.8 (2.7) | 87.3 (4.2) | 88.9 (3.0) | 83.3 (6.2) |
| RF | 89.8 (3.3) | 89.6 (4.4) | 85.1 (7.6) | 89.9 (3.5) | 89.4 (2.8) | 81.9 (5.6) |
| kNN | 85.3 (3.7) | 89.3 (3.4) | 85.5 (3.2) | 85.0 (3.1) | 89.0 (4.1) | 75.9 (6.1) |

The adaptive classification method may further be applied to WS segmentation as shown in FIG. 2. The GP dataset is used as the training data for a leave-one-out cross-validation procedure: segmentation in the WS image $W_i$ is performed using the labeled GPs of slides other than $W_i$ as the pre-built training DB Θ in Algorithm 1 (FIG. 2B). The process may be repeated for all 27 WS images in the DB.

Based on the GP classification results in Table 1, mRMR and the hierarchical strategy for WS segmentation may be used as they provide competitive classification accuracy at low computation cost. The classifiers to be used are RF (for the first classification stage) and kNN (for the refinement classification stage), which may be selected after competitive validations similar to those in Table 1, but after comparing the results after the adaptive step. It may be hypothesized that the external DB is large and contains large feature variation for which an ensemble classifier as RF is more appropriate, while the internal DB is smaller and contains lower feature variance for which a simpler classifier as kNN is more appropriate. Using the segmentation ground truth (provided by an expert observer) for 7 WS images, one may compute the segmentation accuracy for each tissue type by the Jaccard Index (JI). Let $S_t$ and $G_t$ denote the automatic segmentation result and segmentation ground truth for a tissue type t in a WS image Wi, $$JI(S_t,G_t)=|S_t \cap G_t|/|S_t \cap G_t|.$$

with $JI \in [0, 1]$, a greater value of JI corresponds to a better segmentation result. In Table 2 below, the average JI values of the seven WS images for each tissue type obtained by the conventional method (which only performs the first classification stage in Algorithm 1) are compared with the proposed adaptive classification method. Further, the overall segmentation accuracy (by considering all tissue types) for Wi is computed as:

$$SA = \frac{|\{l(p) \mid l(p) = g(p)\}|}{|W_i|},$$

where $l(p)$ and $g(p)$ denote the assigned label and ground truth label of pixel p, and $|\cdot|$ denotes the cardinality of a set. The average SA values for the seven WS images obtained by the conventional and the proposed methods are 72% and 74%, respectively. These evaluations show the improved performance of the proposed method over the conventional method.

TABLE 2

Average JI values of the conventional classification method and the adaptive classification method for the five tissue types of interest.

| Method | Liver | Tumor | Necrosis | LAs | Stroma |
| --- | --- | --- | --- | --- | --- |
| Conventional classification | 0.50 | 0.31 | 0.54 | 0.44 | 0.44 |
| Adaptive classification | 0.54 | 0.33 | 0.58 | 0.45 | 0.44 |

From the experimental results, it was observed that the GP classification accuracies obtained for the GP dataset (Table 1) are higher than the segmentation accuracies (SA values) because the WS image, and not the GP dataset contains the transitive tissue regions (confusing regions). The neighborhood of the GPs in these transitive regions contains more than one tissue types, which makes them more difficult to classify. The SA values are higher than the JI values, which is expected for a five-class segmentation problem with each class contributing to the false negative areas of all other classes. Further, the second-stage classifier $\Theta$ was empirically chosen as k-nearest-neighbor. The GP dataset was used as the pre-built DB $\mathcal{F}^*$ (see FIG. 2B) in the leave-one-out cross validation procedure: segmentation in the WS image Wi was performed using the labeled GPs of slides other than Wi as $\Theta$.

Figure 5:
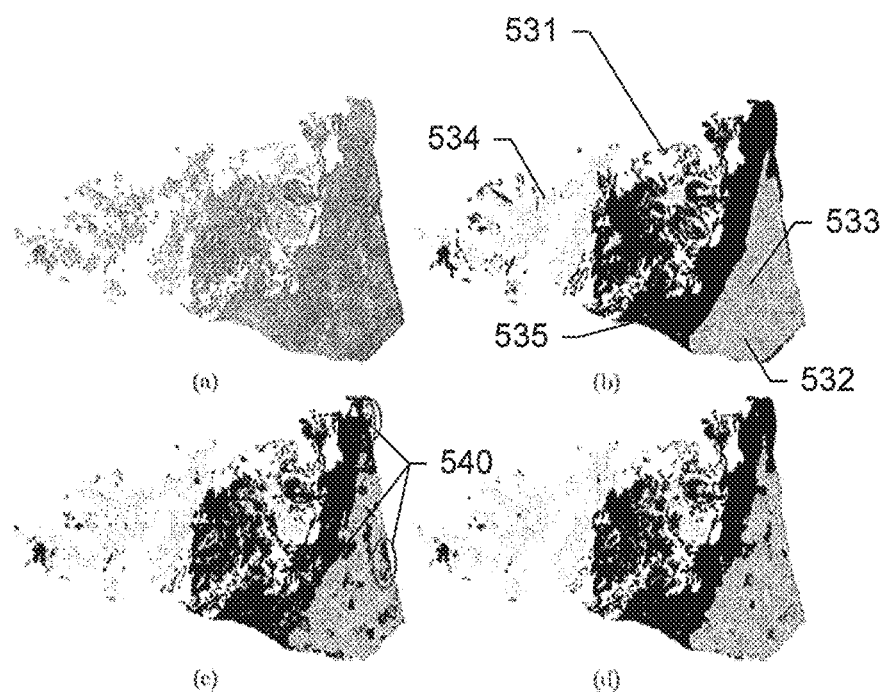
FIGS. 5A-D illustrate whole slide segmentation results, according to exemplary embodiments of the subject disclosure.

FIGS. 5A-5D illustrate whole slide (WS) segmentation results, according to exemplary embodiments of the subject disclosure. FIG. 5A depicts an input WS image of size 18,500×17,200 pixels. FIG. 5B depicts a segmentation ground truth where the differently-shaded regions respectively depict tumor 531, liver 532, LAs 533, necrosis 534, and stroma 535 regions, respectively. FIG. 5C depicts a segmentation result using the conventional method. FIG. 5D depicts the segmentation result using the proposed adaptive classification method. Some of the misclassified regions 540 in FIG. 5C are shown as corrected in FIG. 5D.

Using the segmentation ground truth (provided by an expert observer), the classification accuracies may be computed for each tissue type $t_j$ ($j \in [1,5]$) in the high confidence regions ($x^h$), and the low confidence regions before and after applying the reclassification stage (the respective classified labels are $l(x_i)$ and $l^*(x_i)$, where $x_i \in x^l$). These accuracies, denoted as $A_1$, $A_2$, and $A_3$, respectively, are computed as:

$$A_k = \frac{|\{x_i \in S_k \mid l_k(x_i) = g(x_i) = t_j\}|}{|S_k|} \quad (k = [1, 3])$$

where $g(x_i)$ denote the ground truth label of pixel $x_i$ in the WS image, $S_1 = x^h$, $S_2 = S_3 = x^l$, $h(x_i) = l_2(x_i) = l(x_i)$, $l_3(x_i) = l^*(x_i)$. The average values of $A_1$, $A_2$, and $A_3$ over all WS images for each of the five tissue types are shown in Table 3.

TABLE 3

Classification accuracies in the high confidence regions ($A_1$), and low confidence regions before ($A_2$) and after the reclassification stage ($A_3$).

| Accuracy | Normal Liver | LAs | Tumor | Necrosis | Stroma |
| --- | --- | --- | --- | --- | --- |
| $A_1$ | 0.76 | 0.55 | 0.81 | 0.76 | 0.74 |
| $A_2$ | 0.52 | 0.33 | 0.42 | 0.55 | 0.58 |
| $A_3$ | 0.56 | 0.34 | 0.44 | 0.60 | 0.66 |

Figure 6:
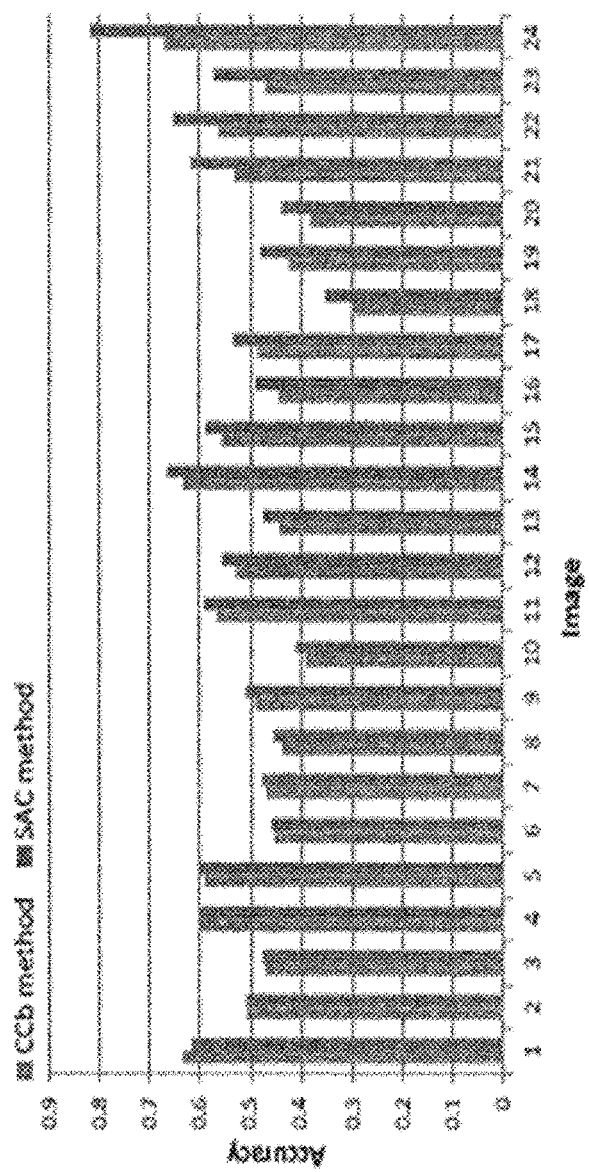
FIG. 6 illustrates the classification accuracies of the prior art ($A_2$ values) versus the disclosed method ($A_3$ values) in the low confidence regions computed for each of 24 whole slide images, according to an exemplary embodiment of the subject disclosure.

Moreover, the average $A_2$ and $A_3$ values are plotted over all tissue types for each of the 24 WS images as depicted in FIG. 6. In this experimental embodiment, the following observations are obtained: (i) $A_1$ values are consistently higher than $A_2$ values, indicating that the high confidence regions selected by the RF classifier are reliable regions in the WS image, and are suitable for the adaptive DB, (ii) $A_3$ values are higher than $A_2$ values, indicating the usefulness of the two-step adaptive classification method in improving the classification results in the presence of inter-slide tissue variability, (iii) as shown in FIG. 6, the two-step adaptive classification method almost always improves result of the prior art methods (improvement is obtained for 23 out of 24 images).

Therefore, a comprehensive framework is provided to address the tissue image segmentation problem in general, and the tissue segmentation in H&E stained sections of liver in particular. Different types of features are extracted from different structural image channels (obtained using a color deconvolution procedure and conversion to Lab color space), and used to describe the tissue structures. To perform segmentation, an adaptive classification method includes first performing GP classification using a pre-built training database, and then using classified GPs with high confidence scores to refine the pre-built training database, thereby generating an adaptive training database that is more appropriate to re-classify the low confidence GPs. Such an adaptive training database is individually generated for each new slide, and due to the large size of the input WS images, a high number of high confidence GPs is expected for each slide from the first classification stage, which makes the training set refinement more reliable.

The foregoing disclosure of the exemplary embodiments of the subject disclosure has been presented for purposes of illustration and description. It is not intended to be exhaustive or to limit the novel features to the precise forms disclosed. Many variations and modifications of the embodiments described herein will be apparent to one of ordinary skill in the art in light of the above disclosure. The scope of the subject disclosure is to be defined only by the claims appended hereto, and by their equivalents.

Electronic processing devices typically include known components, such as a processor, an operating system, system memory, memory storage devices, input-output controllers, input-output devices, and display devices. It will also be understood by those of ordinary skill in the relevant art that there are many possible configurations and components of an electronic processing device and may also include cache memory, a data backup unit, and many other devices. Examples of input devices include a keyboard, a cursor control devices (e.g., a mouse), a microphone, a scanner, and so forth. Examples of output devices include a display device (e.g., a monitor or projector), speakers, a printer, a network card, and so forth. Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provide one or more graphical representations to a user. Interfaces are typically enabled to accept user inputs using means of selection or input known to those of ordinary skill in the related art. The interface may also be a touch screen device. In the same or alternative embodiments, applications on an electronic processing device may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft .NET framework.

Those of ordinary skill in the related art will appreciate that interfaces may include one or more GUI's, CLI's or a combination thereof.

A processor may include a commercially available processor such as a Celeron, Core, or Pentium processor made by Intel Corporation, a SPARC processor made by Sun Microsystems, an Athlon, Sempron, Phenom, or Opteron processor made by AMD Corporation, or it may be one of other processors that are or will become available. Some embodiments of a processor may include what is referred to as multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows type operating system from the Microsoft Corporation; the Mac OS X operating system from Apple Computer Corp.; a Unix or Linux-type operating system available from many vendors or what is referred to as an open source; another or a future operating system; or some combination thereof. An operating system interfaces with firmware and hardware in a well-known manner, and facilitates the processor in coordinating and executing the functions of various programs that may be written in a variety of programming languages. An operating system, typically in cooperation with a processor, coordinates and executes functions of the other components of an electronic processing device. An operating system also provides scheduling, input-output control, file and data management, memory management, and communication control and related services, all in accordance with known techniques.

System memory may include any of a variety of known or future memory storage devices that can be used to store the desired information and that can be accessed by an electronic processing device. Digital storage media may include volatile and non-volatile, removable and non-removable media implemented in any method or technology for storage of information such as digitally encoded instructions, data structures, program modules, or other data. Examples include any commonly available random access memory (RAM), read-only memory (ROM), electronically erasable programmable read-only memory (EEPROM), digital versatile disks (DVD), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium such as, respectively, a compact disk, magnetic tape, removable hard disk, USB or flash drive, or floppy diskette. Any of these program storage media, or others now in use or that may later be developed, may be considered a program product. As will be appreciated, these program storage media typically store a software program and/or data. Software programs, also called control logic, typically are stored in system memory and/or the program storage device used in conjunction with memory storage device. In some embodiments, a program product is described comprising a digital storage medium having control logic (software program, including program code) stored therein. The control logic, when executed by a processor, causes the processor to perform functions described herein. In other embodiments, some functions are implemented primarily in hardware using, for example, a hardware state machine.

Implementation of the hardware state machine so as to perform the functions described herein will be apparent to those skilled in the relevant arts. Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of an electronic processing device communicate with each other via a system bus. Some embodiments of an electronic processing device may communicate with some functional elements using network or other types of remote communications. As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor, in a known manner into system memory, or cache memory, or both, as advantageous for execution. Also, an electronic processing device may include one or more library files, experiment data files, and an internet client stored in system memory. For example, experiment data could include data related to one or more experiments or assays, such as detected signal values, or other values associated with one or more sequencing by synthesis (SBS) experiments or processes. Additionally, an internet client may include an application enabled to access a remote service on another electronic processing device using a network and may for instance comprise what are generally referred to as "Web Browsers". In the present example, some commonly employed web browsers include Microsoft Internet Explorer available from Microsoft Corporation, Mozilla Firefox from the Mozilla Corporation, Safari from Apple Computer Corp., Google Chrome from the Google Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that may employ what is commonly referred to as a TCP/IP protocol suite to communicate. A network may include a network comprising a worldwide system of interconnected networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

Figure 7A:
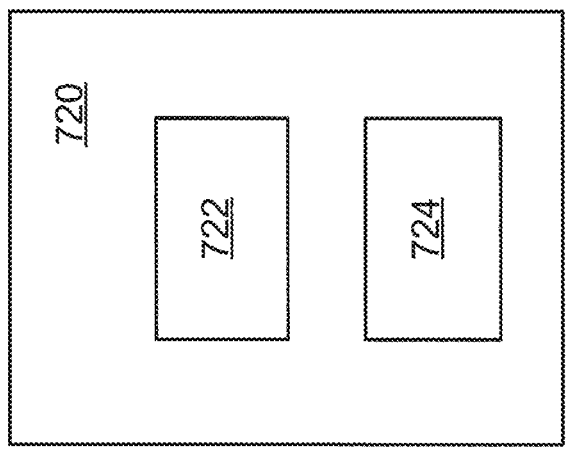
FIG. 7a schematically shows details of the image region classifier module shown in FIG. 7.
Figure 7:
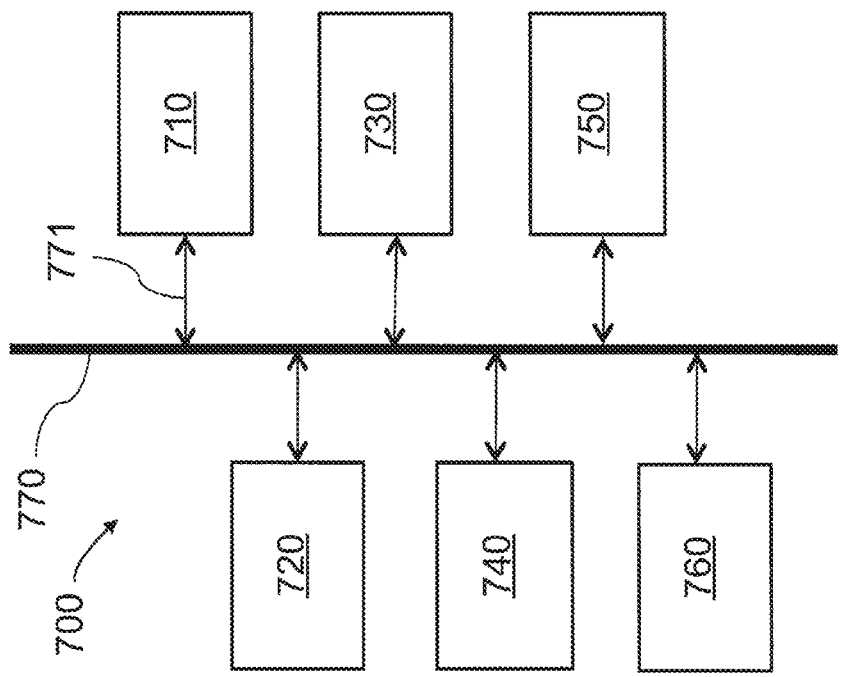
FIG. 7 schematically shows an embodiment of a tissue analysis system.

FIG. 7 schematically shows an embodiment of a tissue analysis system 700 in accordance with the present disclosure, e.g. as described above. In the illustrated embodiment, tissue analysis system 700 comprises an image region identifier module 710, an image region classifier module 720, a database modifier module 730, an image region reclassifier module, an optional tissue imaging device 750, an optional data storage system 760, an optional tissue staining device 770 and a communication bus 780 comprising a plurality of communication links 781 (for the sake of legibility, only one of the communication links bears a reference sign). Communication bus 780 and the communication links 781 communicatively interconnect the aforementioned components 710-770.

FIG. 7a schematically shows details of image region classifier module 720 shown in FIG. 7. In the illustrated embodiment, image region classifier module 720 comprises an optional support vector machine 722 as well as an optional image channel extractor 724. Any of support vector machine 722 and image channel extractor 724 may be communicatively interconnected with each other and with any of the aforementioned components 710-770 via communication bus 780 and communication links 781.

FIG. 8 schematically shows a flow diagram 800 of an embodiment of a tissue analysis method in accordance with the present disclosure, e.g. as described above. In the illustrated embodiment, flow diagram 800 comprises an optional step 810 of staining a tissue sample, an optional step 820 of imaging the (stained) tissue sample, a step 830 of receiving image data, a step 840 of generating image region data, a step 850 of classifying an image region, a step 860 of determining a confidence score, a step 870 of effecting modification of a database, a step 880 of reclassifying an image region and a step 890 of outputting a reclassified tissue type.

FIG. 8a schematically shows details of step 860 shown in FIG. 8. In the illustrated embodiment, step 860 comprises an optional step 862 of performing a support vector machine operation.

FIG. 8b schematically shows details of step 880 shown in FIG. 8. In the illustrated embodiment, step 880 comprises an optional step 882 of weighting data.

FIG. 8c schematically shows an embodiment of step 850 shown in FIG. 8. In the illustrated embodiment, step 850 comprises an optional step 854 of extracting at least one feature from an image region.

FIG. 8d schematically shows an embodiment of step 850 shown in FIG. 8. In the illustrated embodiment, step 850 comprises an optional step 852 of separating an image region into component channels and an optional step 854 of extracting at least one feature from an image region.

In the present disclosure, the verb "may" is used to designate optionality/noncompulsoriness. In other words, something that "may" can, but need not. In the present disclosure, the verb "comprise" may be understood in the sense of including. Accordingly, the verb "comprise" does not exclude the presence of other elements/actions. In the present disclosure, relational terms such as "first," "second," "top," "bottom" and the like may be used solely to distinguish one entity or action from another entity or action without necessarily requiring or implying any actual such relationship or order between such entities or actions.

In the present disclosure, the term "any" may be understood as designating any number of the respective elements, e.g. as designating one, at least one, at least two, each or all of the respective elements. Similarly, the term "any" may be understood as designating any collection(s) of the respective elements, e.g. as designating one or more collections of the respective elements, a collection comprising one, at least one, at least two, each or all of the respective elements. The respective collections need not comprise the same number of elements.

In the present disclosure, the expression "at least one" is used to designate any (integer) number or range of (integer) numbers (that is technically reasonable in the given context). As such, the expression "at least one" may, inter alia, be understood as one, two, three, four, five, ten, fifteen, twenty or one hundred. Similarly, the expression "at least one" may, inter alia, be understood as "one or more," "two or more" or "five or more."

In the present disclosure, expressions in parentheses may be understood as being optional. As used in the present disclosure, quotation marks may emphasize that the expression in quotation marks may also be understood in a figurative sense. As used in the present disclosure, quotation marks may identify a particular expression under discussion.

In the present disclosure, many features are described as being optional, e.g. through the use of the verb "may" or the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

Further, in describing representative embodiments of the subject disclosure, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the subject disclosure should not be limited to the performance of their steps in the order written, and one skilled in the art can readily appreciate that the sequences may be varied and still remain within the spirit and scope of the subject disclosure.

The invention claimed is:

1. A tissue analysis system comprising:
   a processor configured to act as:
      an image region identifier module configured to receive image data representative of an at least two-dimensional image of a tissue sample and to output image region data that identifies a plurality of subsets of said image data, each image data subset being representative of a unique, spatially contiguous region of said image;
      an image region classifier module that is configured to classify, for a plurality of said image regions, the respective image region as one of a plurality of tissue types using the respective image data subset for querying a database of tissue characteristics and to determine a confidence score indicative of a confidence of said classifying of the respective image region;
      a database modifier module that, for a plurality of said image regions having a confidence score falling within a first range, is configured to effect modification of said database such that the resultant modified database comprises data representative of the tissue type classified to the respective image region and tissue characteristic data obtained from the respective image data subset, said first range being a range of confidence scores that includes a confidence score representative of certainty that the classification is correct; and
      an image region reclassifier module that is configured to reclassify, for a plurality of said image regions having a confidence score falling within a second range distinct from said first range, the respective image region as one of said plurality of tissue types using the respective image data subset for querying said modified database and to output said one of said plurality of tissue types as an analysis result, wherein said reclassifying the respective image region to a respective reclassified tissue type comprises weighting data of the respective image data subset and the data obtained from said modified database using: (i) a spatial proximity value indicative of proximity of the respective image region to an image region corresponding to the respective reclassified tissue type in said modified database, (ii) a confidence score corresponding to an image region for the respective reclassified tissue type in said modified database, (iii) a feature similarity value indicative of similarity to an image region corresponding to the respective reclassified tissue type in said modified database, or (iv) any combination thereof.

2. The tissue analysis system of claim 1, further comprising:
   a tissue imaging device configured to image a tissue sample to obtain raw image data, wherein said received image data is obtained from said raw image data.

3. The tissue analysis system of claim 1, further comprising:
   a tissue staining device configured to stain said tissue sample to obtain a stained tissue sample; and
   a tissue imaging device configured to image said stained tissue sample to obtain said image data, wherein said received image data is obtained from raw image data.

4. The tissue analysis system of claim 1, further comprising:
   a data storage system configured to store said database, wherein said database comprises, for each of a plurality of tissue image regions, data representative of an at least two-dimensional image of tissue, data representative of at least one tissue feature, data representative of a tissue type and data representative of a confidence score, wherein the database is a pre-built first training database that is used for the image classification and confidence score determination by the image region classifier module, wherein the database modifier module is configured to generate a second training database that is constituted by the data representative of the tissue type classified to the image regions and the tissue characteristic data obtained from the image data subsets of the plurality of said image regions having a confidence score falling within the first range and to combine the first and the second training database to provide the modified database.

5. The tissue analysis system of claim 1, wherein said image region classifier module comprises a support vector machine and is configured to use an output of said support vector machine for determining said confidence score.

6. The tissue analysis system of any claim 1, wherein said classifying the respective image region comprises extracting at least one feature from the respective image region using the respective image data subset and said data obtained from said database, said feature belonging to the group consisting of textural features, biological features, intensity features, gradient features, Gabor features, co-occurrence features, and nuclei features.

7. The tissue analysis system of claim 1, wherein said reclassifying the respective image region comprises weighting data of the respective image data subset and the data obtained from said modified database using the confidence score corresponding to an image region for the respective reclassified tissue type in said modified database.

8. The tissue analysis system of claim 1, wherein:
said image region classifier module comprises an image channel extractor; and
said classifying the respective image region comprises separating, using said image channel extractor, at least the respective region of said image into one or more component channels and extracting at least one feature from the respective image region using any of said one or more component channels of the respective image region and said data obtained from said database, wherein said feature belongs to the group consisting of textural features, biological features, intensity features, gradient features, Gabor features, co-occurrence features, and nuclei features, and said one or more component channels belong to the group consisting of a hematoxylin channel, an eosin channel, and a luminance channel.

9. The tissue analysis system of claim 1, wherein:
said image region classifier module is configured to build classifier logic using data of said database and to apply, for each of said image regions, said classifier logic to said image data subset of the respective image region to determine the respective tissue type and the respective confidence score;
said database modifier module is configured to find those image regions having a confidence score falling within said first range and those image regions having a confidence score falling within said second range and to combine said database and the respective tissue types and the respective image data subset of said image regions found to have a confidence score falling within said first range to obtain said modified database;
said image region reclassifier module is configured to modify said classifier logic by means of machine learning using data of said modified database and to apply, for each of said image regions found to have a confidence score falling within said second range, said modified classifier logic to said image data subset of the respective image region to determine the respective reclassified tissue type;
said system is configured to output the respective tissue type of each of said image regions found to have a confidence score falling within said first range and the respective reclassified tissue type of each of said image regions found to have a confidence score falling within said second range as a classification result.

10. The tissue analysis system claim 1, wherein:
said database modifier module is configured to determine, for each of said plurality of tissue types and only for those image regions having a confidence score falling within said first range, the total number of image regions having the respective tissue type, and to effect said modification of said database only for those tissue types for which the total number of image regions having the respective tissue type exceeds a respective threshold number for the respective tissue type.

11. The tissue analysis system of claim 10, wherein, for those tissue types for which the total number of image regions having the respective tissue type exceeds a respective threshold number for the respective tissue type, said database modifier module is configured to effect said modification of said database such that said modified database contains solely tissue characteristic data obtained from the respective image data subsets.

12. A tissue analysis method, comprising:
receiving image data representative of an at least two-dimensional image of a tissue sample;
generating image region data that identifies a plurality of subsets of said image data, each image data subset being representative of a unique, spatially contiguous region of said image;
classifying, for a plurality of said image regions, the respective image region as one of a plurality of tissue types using the respective image data subset and using data obtained from a database of tissue characteristics;
determining a confidence score indicative of a confidence of said classifying of the respective image region;
effecting, for a plurality of said image regions having a confidence score falling within a first range, modification of said database such that the resultant modified database comprises data representative of the tissue type classified to the respective image region and tissue characteristic data obtained from the respective image data subset, said first range being a range of confidence scores that includes a confidence score representative of certainty that the classification is correct;
reclassifying, for a plurality of said image regions having a confidence score falling within a second range distinct from said first range, the respective image region as one of said plurality of tissue types using the respective image data subset for querying said modified database, wherein said reclassifying to a respective reclassified tissue type comprises:
weighting data of the respective image data subset and the data obtained from said modified database using: (i) a spatial proximity value indicative of proximity of the respective image region to an image region corresponding to the respective reclassified tissue type in said modified database, (ii) a confidence score corresponding to an image region for the respective reclassified tissue type in said modified database, (iii) a feature similarity value indicative of similarity to an image region corresponding to the respective reclassified tissue type in said modified database, or (iv) any combination thereof; and
outputting, for at least one of said image regions having the confidence score falling within the second range distinct from said first range, the reclassified tissue type of the respective image region.

13. The tissue analysis method of claim 12, further comprising:
imaging a tissue sample to obtain raw image data, wherein said received image data is obtained from said raw image data.

14. The tissue analysis method of claim 12, further comprising:
staining said tissue sample to obtain a stained tissue sample;
imaging said stained tissue sample to obtain raw image data, wherein
said received image data is obtained from said raw image data.

15. The tissue analysis method of claim 12, wherein:
said database comprises, for each of a plurality of tissue image regions, data representative of an at least two-dimensional image of tissue, data representative of at least one tissue feature, data representative of a tissue type and data representative of a confidence score, wherein the database is a pre-built first training database that is used for the image classification and confidence score determination by the image region classifier module, wherein a database modifier module generates a second training database that is constituted by the data representative of the tissue type classified to the image regions and the tissue characteristic data obtained from the image data subsets of the plurality of said image regions having a confidence score falling within the first range and combines the first and the second training database to provide the modified database.

16. The tissue analysis method of claim 12, wherein said determining a confidence score comprises a support vector machine operation.

17. The tissue analysis method of claim 12, wherein said classifying the respective image region comprises extracting at least one feature from the respective image region using the respective image data subset and said data obtained from said database, said feature belonging to the group consisting of textural features, biological features, intensity features, gradient features, Gabor features, co-occurrence features, and nuclei features.

18. The tissue analysis method of claim 12, wherein said reclassifying the respective image region comprises weighting data of the respective image data subset and the data obtained from said modified database using the feature similarity value.

19. The tissue analysis method of claim 12, wherein said classifying the respective image region comprises separating at least the respective region of said image into one or more component channels and extracting at least one feature from the respective image region using any of said one or more component channels of the respective image region and said data obtained from said database, wherein
    said feature belongs to the group consisting of textural features, biological features, intensity features, gradient features, Gabor features, co-occurrence features, and nuclei features, and said one or more component channels belong to the group consisting of a hematoxylin channel, an eosin channel and a luminance channel.

20. The tissue analysis method of claim 12, further comprising:
    building classifier logic using data of said database;
    applying, for each of said image regions, said classifier logic to said image data subset of the respective image region to determine the respective tissue type and the respective confidence score;
    finding those image regions having a confidence score falling within said first range and those image regions having a confidence score falling within said second range;
    combining said database and the respective tissue types and the respective image data subset of said image regions found to have a confidence score falling within said first range to obtain said modified database;
    modifying said classifier logic by means of machine learning using data of said modified database;
    applying, for each of said image regions found to have a confidence score falling within said second range, said modified classifier logic to said image data subset of the respective image region to determine the respective reclassified tissue type; and
    outputting the respective tissue type of each of said image regions found to have a confidence score falling within said first range and the respective reclassified tissue type of each of said image regions found to have a confidence score falling within said second range as a classification result.

21. The tissue analysis method of claim 12, further comprising:
    determining, for each of said plurality of tissue types and only for those image regions having a confidence score falling within said first range, the total number of image regions having the respective tissue type, wherein said modification of said database is only effected for those tissue types for which the total number of image regions having the respective tissue type exceeds a respective threshold number for the respective tissue type.

22. The tissue analysis method of claim 21, wherein, for those tissue types for which the total number of image regions having the respective tissue type exceeds a respective threshold number for the respective tissue type, said modification of said database is effected such that said modified database contains solely tissue characteristic data obtained from the respective image data subsets.

23. A method for segmentation of a tissue image being implemented by an electronic device, comprising:
    identifying grid points in the tissue image;
    classifying the grid points as one of a plurality of tissue types, and generating classified grid points based on a database of known characteristics of tissue types;
    assigning each classified grid point of the classified grid points a high confidence score or a low confidence score;
    modifying the database of known characteristics of tissue types based on the grid points that were assigned a high confidence score, and generating a modified database; and
    reclassifying the grid points that were assigned a low confidence score based on the modified database, wherein reclassifying a grid point to a respective reclassified tissue type comprises:
        weighting data of the respective grid point and the data obtained from the modified database using: (i) a spatial proximity value indicative of proximity of the respective grid point to grid point corresponding to the respective reclassified tissue type in the modified database, (ii) a confidence score corresponding to a grid point for the respective reclassified tissue type in the modified database, (iii) a feature similarity value indicative of similarity to a grid point corresponding to the respective reclassified tissue type in the modified database, or (iv) any combination thereof.

24. A non-transitory computer-readable medium storing instructions which, when executed by a processor, cause the processor to:
    assign an image patch of a tissue sample with a confidence score based on a comparison with a database of known features associated with said tissue sample; and
    refine the confidence score for the image patch based on a comparison of the image patch with one or more high-confidence image patches from the same tissue sample;
    wherein:
        the high-confidence image patches are stored in a database of high-confidence image patches associated with the tissue sample, and
        the comparison with the one or more high-confidence image patches comprises weighting data of the image patch and the one or more high-confidence image patches in the database using: (i) a spatial proximity value indicative of proximity of the image patch to a high-confidence image patch of the one or more high-confidence image patches in the database, (ii) a confidence score corresponding to a high-confidence image patch of the one or more high-confidence image patches in the modified database, (iii) a feature similarity value indicative of similarity to a high-confidence image patch of the one or more high-confidence image patches in the database, or (iv) any combination thereof.

* * * * *